United States Patent [19]

Barrett

[11] Patent Number: 5,340,537

[45] Date of Patent: Aug. 23, 1994

[54] TEMPERATURE INDICATING COMPOSITIONS

[75] Inventor: Richard B. Barrett, Chatham, N.J.

[73] Assignee: Big Three Industries, Inc., South Planfield, N.J.

[21] Appl. No.: 48,777

[22] Filed: Apr. 16, 1993

[51] Int. Cl.$^5$ .................... A61L 2/04; B41M 5/18
[52] U.S. Cl. .................... 422/26; 422/28; 503/208; 503/214; 503/221; 503/222; 503/225; 524/594; 428/913; 428/914
[58] Field of Search .......... 503/208, 214, 221, 222, 503/225; 524/594; 252/408.1; 428/913, 914; 422/26, 28

[56] References Cited

U.S. PATENT DOCUMENTS

| | | | |
|---|---|---|---|
| 3,539,375 | 11/1970 | Baum | 117/36.2 |
| 4,155,895 | 5/1979 | Rohowetz et al. | 260/33.4 R |
| 4,179,397 | 12/1979 | Rohowetz et al. | 422/26 |
| 4,228,222 | 10/1980 | Murakami et al. | 428/500 |
| 4,287,264 | 9/1981 | Marginean | 428/514 |
| 4,289,535 | 9/1981 | Marginean et al. | 106/19 |
| 4,336,067 | 6/1982 | Shackle et al. | 503/208 |
| 4,568,956 | 2/1986 | Matsushita et al. | 428/913 |
| 4,612,270 | 9/1986 | Pampalone et al. | 430/273 |
| 4,647,952 | 3/1987 | Pokora et al. | 346/210 |
| 4,868,151 | 9/1989 | Satake et al. | 503/221 |
| 4,985,390 | 1/1991 | Nakashima et al. | 503/208 |
| 5,023,164 | 6/1991 | Brunsvold et al. | 430/270 |
| 5,087,659 | 2/1992 | Fujisawa | 422/26 |
| 5,112,798 | 5/1992 | Miyauchi | 503/225 |

FOREIGN PATENT DOCUMENTS

| | | |
|---|---|---|
| 0434420 | 6/1991 | European Pat. Off. . |
| 3176180 | 7/1988 | Japan . |

*Primary Examiner*—Paul R. Michl
*Assistant Examiner*—Tae H. Yoon
*Attorney, Agent, or Firm*—Lerner, David, Littenberg, Krumholz & Mentlik

[57] ABSTRACT

Temperature indicating compositions of dispersions in an aqueous binder of a color changing electron donating compound having a melting point greater than about 300° F. and a polymeric electron accepting resin reactive with the electron donating compound to produce a visible and permanent color change and having a $T_g$ and non-volatility effective to provide a color change to coatings containing the composition upon exposure to a predetermined heat history. Temperature indicating materials are also disclosed containing a support coated on at least one surface thereof with the temperature indicating composition to the present invention.

18 Claims, No Drawings

TEMPERATURE INDICATING COMPOSITIONS

BACKGROUND OF THE INVENTION

The present invention relates to moisture stable temperature indicating compositions that produce a visible and permanent color change upon exposure to a predetermined heat history. The present invention also relates to indicator materials containing coatings of the temperature indicating compositions on at least one surface of a suitable support. In particular, the present invention relates to temperature indicating compositions and coatings thereof that do not fully undergo a color change until the coating has been exposed to saturated steam at a temperature of 250° F. for more than 3 minutes. They do, however, signal fully after 20 minutes in the presence of saturated steam at 250° F. Products presently available to meet this need suffer from several deficiencies. Many are formulated with metallic salts such as carbonates of copper or lead. Color development comes from the reaction of a sulfidic component, present as sulfur, thiosulfate, or a sulfur containing organic compound (U.S. Pat. Nos. 3,471,222 and 3,523,011) to form a black metallic sulfide.

The resulting deficiencies include:
(1) a limitation in the final signal color because of the blackness of the metallic sulfide;
(2) a poor resistance to elevated, but not unusual, levels of temperature and humidity during transport and storage. Copper-based inks are particularly susceptible to premature signaling under these "tropical" conditions; and
(3) materials printed with lead containing inks are increasingly unsuitable for disposal in land fills, or by incineration, in countries whose environmental sensitivities and current legislation are significantly more restrictive than in earlier times.

The products that will be further described below overcome these deficiencies by (1) being available in a range of final signal colors, (2) being resistant to signaling during "tropical" storage conditions and (3) being completely free of environmentally regulated compounds of lead or copper.

The color-changing reaction between an electron donating compound such as a prodye or chromogen and an electron accepting compound, typically a phenolic compound, has been widely used in the field of duplication and printing processes for the preparation of heat sensitive coating compositions, for the production of heat sensitive paper for thermal printing devices (see e.g., U.S. Pat. No. 4,289,535, and the patents cited therein, as well as U.S. Pat. Nos. 4,287,264, 4,228,222 and 3,539,375). This color-changing reaction has also been widely used in the fields of medicine and food processing for the production of heat sensitive compositions suitable for coating on the surface of supports to form sterilization indicators (see, e.g., U.S. Pat. No. 5,087,659, 4,155,895 and 4,179,397).

Coatings of such heat-sensitive compositions are intended to show a distinct difference in color among unprocessed and completely processed packages or foodstuffs. This provides a positive and visible indication that the sterilization process has in fact been carried out.

As discussed in the above-cited U.S. Pat. Nos. 4,287,264 and 4,289,535, state-of-the-art compositions combining an electron donating prodye or chromogen compound with an electron accepting phenolic compound suffer from a tendency to undergo premature color change which is attributable to a lack of environmental stability, particularly to heat and moisture (i.e., humidity). Unthermostated shipping and warehouse storage conditions, as well as tropical climates, are well-known as causes of premature color-change.

While premature color-change is an inconvenience for the thermal printing industry because it ruins shipments of heat-sensitive paper, the phenomena is a critical problem for the medical profession and food processing industry because the premature color change creates a false-positive indication that medical and surgical goods have been processed or sterilized. There remains a need for temperature indicator compositions that undergo a visible and permanent color change under sterilization conditions, yet at the same time do not undergo premature color change upon exposure to elevated shipping and storage temperatures or the heat and humidity of tropical climates.

SUMMARY OF THE INVENTION

The present invention incorporates the discovery that premature color change occurs in temperature indicating compositions prepared with low-melting or volatile electron accepting compounds. It has been discovered that as conditions approach the electron accepting compound's melting point (if crystalline) or $T_g$ (if amorphous), or following generation of significant partial vapor pressure, electron transfer can occur between the electron donating compound and the electron accepting compound in the presence of humidity or other ambient vapors which solubilize the chromogenic compounds, resulting in a premature color change. Once the temperature exceeds the melting point or $T_g$, or sufficient partial vapor pressure is present, electron transfer can occur without ambient moisture. The present invention solves the problem of premature color change by utilizing polymeric electron accepting resins having a $T_g$ and non-volatility effective to prevent premature color change.

The polymeric electron accepting resins can be dispersed in aqueous binders with electron donating compounds that change color upon electron donation. The electron accepting resins are selected so that the dispersions can then be formed into coatings that do not change color until the coating has been exposed to a predetermined heat history such as saturated steam at 250° F. for more than 20 minutes.

It has also been discovered that should the prodye melt or develop significant partial vapor pressure of its own, premature color development may also occur. It has been found that prodyes with melting points in excess of 300° F. are suitable for use in this invention.

Therefore, in accordance with the present invention, a temperature indicating composition is provided that is a dispersion of a color changing electron donating compound having a melting point greater than 300° F., and a polymeric electron accepting resin reactive with the electron donating compound to produce a visible and permanent color change, both in an aqueous binder. The resin must have a $T_g$ and non-volatility effective to provide a color change to coatings containing the composition upon exposure to a predetermined heat history but not prior to that exposure. Preferably, the volatility of the electron donating compound and the polymeric electron accepting resin is effective to prevent coatings containing the composition from fully changing color before the coating has been exposed to saturated steam at a temperature greater than 250° F. for more than 20 minutes.

The compositions of the present invention are free of undesirable heavy metals and sulfidic compounds. Preferred compositions are also free of volatile organic compounds and other undesirable solvents.

The compositions of the present invention may be incorporated into paints, inks and other formulations that may be coated onto one or more surfaces of a suitable support to form a temperature indicator material. Therefore, in accordance with the present invention, there is also provided a temperature indicating material including a support coated on at least one surface thereof with the temperature indicator composition of the present invention.

Coatings of preferred temperature indicator compositions of the present invention are color stable when subjected to dry heat at 284° F. for 30 minutes. The coatings are also stable when subjected to 80 percent relative humidity at 149° F. for 266 hours, yet produce a fully developed visible and permanent color change when subjected to saturated steam at 250° F. and 15 psi for 20 minutes or to CHEMICLAVE chemical sterilization agents for 20 minutes at 270° F. and 30–40 psi. The temperature indicator compositions of the present invention and coatings thereof thus provide reliable environmentally stable sterilization processs indicators.

DETAILED DESCRIPTION OF THE PREFERRED EMBODIMENT

The temperature indicating compositions of the present invention contain a dispersion in an aqueous binder of an electron donating compound that changes color upon electron donation and a polymeric electron accepting resin reactive with the electron donating compound to produce a color change.

The electron donating compound is typically a prodye or chromogen that may be colorless to start with and develop a color upon reacting with the electron accepting resin, or the chromogen may be colored to start with and become colorless as the reaction is completed, or it may be a light color and change to a deep or other distinctive color. Once the predetermined threshold exposure conditions are met, the electron donating chromogen is oxidized by the electron accepting resin to develop the full color change.

The electron donating chromogen and polymeric electron accepting resin are dispersed in an aqueous binder. Aqueous binders for coating compositions such as paints or inks are essentially conventional and well-known to those of ordinary skill in the art. In general, the binders are aqueous polymer suspensions or solutions selected to maintain the integrity of the composition coating on selected substrates. Suitable polymers include starch, polyvinyl alcohol, styrene-butadiene rubber and certain acrylics. The preferred binder polymer is polyvinyl alcohol.

The suitable molecular weight range for a given binder polymer is that range within which the polymer can be dissolved or suspended in water. Preferred molecular weights will depend upon the viscosity and solids levels desired for the compositions, which can be readily determined by one of ordinary skill in the art without undue experimentation. Polyvinyl alcohols having a molecular weight between about 30,000 and about 70,000 are suitable for use with the present invention, and molecular weights between about 45,000 and about 65,000 are preferred.

Aqueous binders suitable for use with the present invention will contain between about 3 and about 10 percent by weight of polymer. Between about 4 and about 6 percent by weight of polymer is preferred.

In general, the level of aqueous binder in the temperature indicator compositions of the present invention will range from about 20 to about 50 percent by total dispersion weight and preferably between about 35 and about 45 percent by total dispersion weight. The amount of aqueous binder in the sterilization indicator compositions of the present invention will vary with the coating application and coating thickness desired. Appropriate binder levels for various printing processes and coating thicknesses can be readily determined by one of ordinary skill in the art without undue experimentation.

The polymeric electron accepting resin is selected to produce a visible and permanent color change in a coating of the temperature indicator composition of the present invention upon exposure of the coating to a predetermined heat history. For dry environments, an electron accepting resin is selected having a $T_g$ at or above the temperature to be recorded. The color change of the coating then indicates that the predetermined temperature has been attained. For purposes of the present invention, "heat history" refers to ambient atmospheric conditions such as moisture, humidity and the presence of CHEMICLAVE chemical sterilizing agents.

For sterilization environments, including saturated steam or chemical sterilization agents, electron transfer between the polymeric electron accepting resin and electron donating compound will occur somewhat below the $T_g$ of the electron accepting resin. Accordingly, an electron accepting resin should be selected having a $T_g$ greater than the temperature condition desired to be recorded. If a combination of temperature and time is desired, that is, if the color change is to indicate that a predetermined temperature was attained and held for a predetermined time period, then an even higher $T_g$ electron accepting resin should be employed.

For example, steam autoclave sterilization of medical equipment is often performed for 20 minutes using saturated steam at 15 psi (250° F.). Temperature indicator coatings of the present invention that will accurately indicate that such a combination of time, saturated steam and temperature had been attained will contain a polymeric electron accepting resin having a $T_g$ greater than 270° F. Preferred electron accepting resins for this end-use application will have a $T_g$ greater than 290° F. Even more preferred electron accepting resins for this end-use application will have a $T_g$ of about 300° F. An electron accepting resin may be selected having a higher $T_g$ than the minimum requirement. This will lead to a lengthening in the time required for full color development. However, the $T_g$ should not be so great as to produce a false-negative result. For steam or chemical sterilization, the $T_g$ preferably should not exceed 350° F.

The polymeric electron accepting resins should also be non-volatile. That is, at below-sterilization temperatures, the polymer should not produce vapors that will react with the electron donating compound to produce a premature color change. The preferred $T_g$ polymers are generally non-volatile. However, lower $T_g$ non-volatile polymers can be readily identified by those of ordinary skill in the art.

Similar considerations apply for sterilization techniques employing certain chemical sterilizing agents, such as the CHEMICLAVE process, which subjects objects to be sterilized to a saturated solvent vapor environment for 20 minutes at 275° F. and 20 psi. The solvent vapor environment contains less than 15 percent water, with the remainder made up of a mixture of alcohols, including ethanol, iso-propyl alcohol, methanol, and approximately 0.25 percent formaldehyde. Temperature indicating compositions containing polymeric electron accepting resins having $T_g$'s suitable for use with steam sterilization are also suitable for use with the CHEMICLAVE process.

Polymeric electron accepting resins suitable for use with the present invention can be readily identified by one of ordinary skill in the art. In general, the compounds are acidic materials such as phenolic resins. Phenolic resins having a $T_g$ suitable for use in sterilization temperature indicator compositions, for example, include the phenolic resins disclosed by U.S. Pat. No. 4,647,952, the disclosure of which is hereby incorporated by reference herein. A commercially available and particularly preferred species of the disclosed resins is Resin HG, a polymer of Bisphenol A, produced by The Mead Corporation of Chillicothe, Ohio.

Another group of phenolic resins having $T_g$'s suitable for use in sterilization temperature indicator compositions are the high purity, high melt point, meta-cresol novolac resins available from Schenectady International of Schenectady, N.Y. Schenectady International's HRJ-2729 and HRJ-12359 meta-cresol novolac resins are particularly preferred. However, essentially any acidic polymeric electron accepting resin having a $T_g$ or vapor pressure effective to promote the color change upon exposure to the predetermined heat history without prematurely changing color is suitable for use in the present invention.

In general, the polymeric electron accepting resin will be present in the temperature indicator compositions of the present invention in amounts ranging from about 2 to about 20 percent by total dispersion weight and preferably from about 5 to about 10 percent by total dispersion weight. As is well-known to anyone skilled in the art, the type of electron accepting resin used, as well as the type of electron donating compound, will vary depending upon the color desired for the temperature indicator composition, either before or after the color change. Likewise, the amount of electron accepting resin, as well as the amount of the electron donating compound, will vary largely depending upon the type of compounds which are used and are the desired shade and intensity of color to be produced in the temperature indicator coatings.

Any of various known chromogenic materials may be used for the electron donating compound of the present invention, provided the chromogenic material has a melting point greater than 300° F. Suitable chromogens include iso benzo xanthanones such as COPIKEM 1, which is available from Hilton Davis Co. of Cincinnati, Ohio, and iso benzo furanones, such as COPIKEM 4 and COPIKEM 20, which are also available from Hilton Davis. Also suitable are PERGASCRIPT BLACK, a diamino fluorane compound and PERGASCRIPT ORANGE, a substituted amino fluorane. Both are available from CIBA-GEIGY of Greensboro, N.C. The disclosed prodye or chromogen electron donating compounds may be used either solely or in combination.

However, essentially any compound having a melting point greater than 300° F. that will donate electrons to the polymeric electron accepting resin with a resulting change in visible color can be used in the present invention. In general, the prodye or chromogen electron donating compound will be present in the temperature indicating composition in amounts ranging from about 1 to about 5 percent by total dispersion weight and preferably from about 1.5 to about 2.5 percent by total dispersion weight.

An important feature of the temperature indicating compositions of the present invention is that neither the polymeric electron accepting resin or the prodye or chromogen electron donating compound require encapsulation in microcapsules. That is, both the electron accepting resin and the electron donating compound are non-encapsulated. Compositions prepared in accordance with the present invention nevertheless will not undergo a color change until the predetermined heat history has been met. By not encapsulating either the electron donating compound or electron accepting resin, an improvement in product cost and an improvement in production efficiency is obtained.

The ratio of the polymeric electron accepting resin and electron donating compound is not critical. A stoichiometric excess of electron accepting resin is preferred to promote the release of electrons from the electron donating compound, and consequently, to promote the color change once the predetermined heat history has been met.

A color change can be produced at temperatures below the effective dry heat signaling temperature of the compositions of the present invention by including in the compositions an additive inert to the electron transfer reaction between the electron donating compound and electron accepting resin and having a melting point slightly below the lower color signaling temperature. Preferred additives have melting points in a range up to 15° F. higher or lower than the lower color signaling temperature. More preferred additives have a melting point in a range up to 10° F. higher or lower than the lower color signalling temperature.

Essentially any crystalline material inert to the electron transfer reaction, having the requisite melting point and capable of forming a medium in which both the electron donating and electron accepting compounds are soluble is suitable for use as the inert additive. While not being bound by any particular theory, it is believed that the additive, at or about its melting point, provides a medium through which the electron transfer can occur.

In general, the inert additive will be present in the temperature indicating composition in amounts ranging from about 5 to about 20 percent by weight of the dispersion. Examples of suitable additives include benzoates, fatty amides and non-polar waxes. Thus, a color change can be produced at 212° F. by adding to the compositions of the present invention an effective amount of octadecanamide (stearic amide), which has a melting point slightly above 212° F.

The temperature indicating compositions of the present invention also include various conventional additives for paint and ink-type coating compositions. For example, pigments such as titanium dioxide are selected to provide hiding power and color enhancement of the signal color. Also among the additives are coloring dyes, which do not change color upon exposure to the predetermined heat history. This permits the modification of the color change. For example, a blue coloring dye can be combined with a chromogen that changes from colorless to red upon electron donation to effect a color change from blue to purple. The selection of dispersion-improving pigments and coloring dyes is essentially conventional and well-understood by those of ordinary skill in the art.

Other conventional additives suitable for use with the compositions of the present invention include surfactants, releasing agents, carriers, lubricants, extenders, biocides, drying agents, dispersing agents, defoamers, rheology and viscosity modifiers, and the like. Such additives are generally present in amounts between about 0.1 and about 5 percent by total dispersion weight and preferably in amounts between about 0.5 and about 3 percent by total dispersion weight.

The temperature indicating compositions of the present invention are prepared by separately forming aqueous dispersions of the polymeric electron accepting resin and the prodye or chromogen electron donating compound. The electron accepting resin dispersion contains the polymeric electron accepting resin, a portion of the water-soluble binder polymer and a portion of any titanium dioxide or other dispersing agent to be utilized. The electron donating compound dispersion contains the prodye or chromogen electron donating compound, the remainder of the water-soluble binder polymer and the remainder of the titanium dioxide or other dispersing agent, if present, as well as any other conventional additive to be utilized. Both dispersions are each separately ground with water, suitably at a concentration of between about 10 and about 50 percent, sufficiently to reduce the solids to an average particle size of several microns, preferably of between about 2 and about 5 microns.

The resulting two dispersions are then mixed together, preferably without heat, into a single temperature indicating coating composition, which may be applied to a suitable support, optionally after being further diluted with an aqueous diluent, compatible with the bulk formulation. Alternatively, the two dispersions may be applied to the support separately to form different layers of coating.

The temperature indicating compositions of the present invention may be coated onto one or more surfaces of various support substrates by conventional coating processes to obtain tape-type, label-type and card-type temperature monitoring articles, such as sterilization monitoring articles. These articles can be coated with an adhesive to adhere them to various substrates. The compositions can also be printed or coated directly onto packages, boxes, cartons, containers and the like to monitor the heat-history of the contents.

Preferred substrates for receiving coatings of the temperature indicating compositions of the present invention, which may be either formed into a tape, label or card that is adhesively applied to a second substrate, or formed into a package, box, carton, container or the like bearing a temperature indicating coating, include polymeric materials, cellulosic materials, metal foils and laminates thereof. Thus, the temperature indicating compositions may be applied to a substrate support such as a carrier, film, web or the like by any number of conventional coating processes known to the art including extrusion coating, printing, and the like. Suitable printing processes include metered doctor roll coating, gravure, flexographic, lithographic, reverse roll coating, slot dye coating, silkscreening, decalcomania, and the like.

The coating may be air dried or the water present may be driven off after application of the coating by conventional oven drying processes. Depending upon the printing process employed, coating thicknesses between about 0.5 and about 2.0 mils are obtained. If heavier coatings are desired, additional coatings of the temperature indicating composition may be alternately applied and dried.

The temperature indicating composition may be applied in a pattern of varying shapes to draw attention to the indicator coating. The powder may also be in the form of a message such as "sterile" that appears upon exposure to the heat history.

The following non-limiting examples set forth below illustrate certain aspects of the invention. All parts and percentages are by weight unless otherwise noted.

EXAMPLES

Temperature indicating compositions in accordance with the present invention were prepared and printed onto a paper substrate. The coatings were then subjected to the tests set forth below.

DRY HEAT:
The coatings were subjected to dry heat at 284° F. for 30 minutes.

TROPICAL STABILITY:
The coatings were subjected to an atmosphere of 80 percent Relative Humidity at 149° F. for 266 hours.

STEAM STERILIZATION:
The coatings were subjected to saturated steam at a temperature of 250° F. at 15 psi for 20 minutes.

CHEMICLAVE STERILIZATION:
The coatings were subjected to CHEMICLAVE vapors for 20 minutes at 275° F. and 20 psi.

SHELF LIFE:
The temperature indicating compositions were sealed in a bottle and stored at 122° F. for 88 hours. After this period of time, a coating was printed and evaluated.

PRINT EVALUATION:
The color values of the printed coatings were evaluated using a Hunter D54 Spectrophotometer. The color lab values, using D65 illumination, were compared. The compared lab values for pairs of prints were used to calculate a $\Delta E$ value, which is a measure of the visual difference between the coatings. Non-exposed coatings were used as the basis of comparison. After exposure to a heat history, a large $\Delta E$ value indicated a high visual contrast.

EXAMPLES 1-5

Five temperature indicating compositions in accordance with the present invention were prepared and each was coated onto a paper support for use as a steam sterilization indicator material. The compounds were prepared from separate dispersions of prodye or chromogen electron donating compounds (Part A) and polymeric electron accepting resins (Part B). General formulations for Part A and Part B are set forth below in Table I:

TABLE I

| Material | Weight Percent |
|---|---|
| Part A: | |
| Electron Donating Compound | 3.87 |

TABLE I-continued

| Material | Weight Percent |
| --- | --- |
| Titanium Dioxide | 15.50 |
| Polyvinyl Alcohol (5% solution) | 41.86 |
| Water | 38.75 |
| Part B: | |
| Polymeric Resin | 14.70 |
| Titanium Dioxide | 11.76 |
| Polyvinyl Alcohol (5% solution) | 36.76 |
| Water | 36.76 |

For each example, the titanium dioxide was Kronos 2020 available from the Kronos Corporation. For each example, the polyvinyl alcohol was Airvol 125 available from Air Products Co.

For each example, Parts A and B were ground separately to produce fine dispersions. The two parts were then combined in equal parts and mixed thoroughly, without heating. The combinations of electron donating compound and polymeric electron accepting resin for each example are identified below.

Example 1

For Example 1, the electron donating compound was COPIKEM 20, an iso benzo furanone. The polymeric electron accepting resin was Resin HG, a polymer of Bisphenol A. Coatings of this composition turned from colorless to red upon exposure to sufficient heat.

Example 2

For this example, the COPIKEM 20 electron donating compound was combined with Schenectady Chemical's HRJ-2729, a meta-cresol novolac resin. Coatings of this composition also changed from colorless to red upon exposure to sufficient heat.

Example 3

In this example, the electron donating compound, which was combined with Schenectady Chemical's HRJ-2729, was COPIKEM 1, an iso benzo xanthanone. Coatings of this composition changed from colorless to blue upon exposure to sufficient heat.

Example 4

In this example, the COPIKEM 1 was combined with the Resin HG. Coatings of this composition changed from colorless to blue.

Example 5

In this example, the COPIKEM 1 was combined with Schenectady Chemical's HRJ-2901, another meta-cresol novolac resin. Coatings of this composition also changed from colorless to blue.

The temperature indicating compositions were then coated onto a variety of generally available papers including bond, xerographic grade and autoclavable kraft. The compositions were laid down using a hand-proofer with a #50 ANILOX Roller and allowed to air dry.

The coatings were then subjected to the above-identified tests. The ΔE values (a measure of contrast between the sterilized and non-sterilized printing) for steam and CHEMICLAVE sterilization are set forth in Table II. Table III sets forth the results (percentage retention of the unsignalled values) for Tropical Stability, Dry Heat and Shelf Life tests. High values indicate high stability.

TABLE II

| Example | ΔE (Steam) | ΔE (Chemiclave) |
| --- | --- | --- |
| 1 | 61.0 | 49.1 |
| 2 | 23.0 | N/A |
| 3 | 17.2 | N/A |
| 4 | 18.5 | N/A |
| 5 | 12.7 | N/A |

N/A - Not Available

TABLE III

| | RESISTANCE TO CHANGE (% UNISGNALED VALUE) | | |
| --- | --- | --- | --- |
| Example | Tropical Stability | Dry Heat | Shelf Life |
| 1 | 82 | 62 | 95 |
| 2 | 93 | 82 | 82 |
| 3 | 98 | 100 | 68 |
| 4 | 82 | 82 | 91 |
| 5 | 95 | 100 | 55 |

N/A - Not Available

Tables II and III demonstrate the superior performance of these formulations. The high values in the dry heat test are significant in view of the fact that the coatings were exposed to 284° F. for 30 minutes. The temperature is 34° F. above, and the time is 50 percent greater than that experienced during steam sterilization. The compositions of the present invention are thus free of the premature color change suffered by prior art prodye-resin coatings which were unsuitable as sterilization indicator compositions.

COMPARATIVE EXAMPLE

Coatings were made of commercially available inks as in Examples 1–5. FWC 566D is a lead-based ink available from Tempil Division of Big Three Industries, South Plainfield, N.J. FRC 743C is a copper-based ink also available from Tempil. The stability of coatings of both inks under tropical conditions was compared to the stability of a coating of the metal-free ink of Example 1. The ΔE values with time are depicted in Table IV:

TABLE IV

| Ink | Hours | | | |
| --- | --- | --- | --- | --- |
| | 0 | 48 | 96 | 266 |
| FWC 566D (Pb) | 50.5 | 48.5 | 46.8 | 17.8 |
| FRC 743C (Cu) | 40.5 | 2.4 | 2 | 2.3 |
| Example 1 | 61 | 49 | 39 | 42 |

Table IV demonstrates another advantage of these inks when compared to presently available commercial steam indicating inks. Note that the ink of Example 1 has the highest ΔE value. More important, after 48 hours, the copper containing ink (FRC 743C) has the appearance of fully sterilized ink. After 266 hours the lead containing ink (FWC 566D) has only 30% (100×17.8/50.5) of its original contrast. Only the ink of Example 1 retains over 65% of its contrast.

As will be readily appreciated, numerous variations and combinations of the features set forth above can be utilized without departing from the present invention as set forth in the claims. Such variations are not to be regarded as a departure from the spirit and scope of the invention, and all such modifications are intended to be included within the scope of the following claims.

What is claimed is:

1. A temperature indicating composition comprising a dispersion in an aqueous binder of a color changing electron donating compound having a melting point greater than about 300° F. and a polymeric electron phenolic accepting resin reactive with said electron donating compound to produce a visible and permanent color change and having a $T_g$ greater than 270° F. and non-volatility such that coatings containing the composition are stable upon exposure to dry heat at 284° F. for 30 minutes yet produce a fully developed visible and permanent color change when subjected to saturated steam at 250° F. for twenty minutes.

2. The temperature indicating composition of claim 1, wherein said phenolic resin comprises a high melt point meta-cresol novolac resin.

3. The temperature indicating composition of claim 1, wherein said phenolic resin comprises a polymer of Bisphenol A.

4. The temperature indicating composition of claim 1, wherein said polymeric electron accepting resin has a $T_g$ greater than about 290° F.

5. The temperature indicating composition of claim 4, wherein said polymeric electron accepting resin has a $T_g$ of about 300° F.

6. The temperature indicating composition of claim 5, wherein said electron donating compound comprises a prodye or chromogen selected from the group consisting of iso benzo furanones, iso benzo xanthanones, di-amino fluoranes and substituted amino fluoranes.

7. The temperature indicating composition of claim 1, wherein said aqueous binder comprises an aqueous polymer solution or suspension.

8. The temperature indicating solution of claim 7, wherein said polymer comprises polyvinyl alcohol.

9. The temperature indicating composition of claim 1, wherein said electron donating compound is non-encapsulated.

10. The temperature indicating composition of claim 1, wherein said polymeric electron accepting resin in non-encapsulated.

11. A temperature indicating material comprising a support coated on at least one surface thereof with the temperature indicating composition of claim 1.

12. The temperature indicating material of claim 11, wherein said coated support surface comprises a material selected from the group consisting of polymeric materials, cellulosic materials, metal foils and laminates thereof.

13. The temperature indicating material of claim 11, wherein said temperature indicating composition is coated on said surface of said support by extrusion coating or printing.

14. The temperature indicating material of claim 13, wherein said printing comprises a printing process selected from the group consisting of metered doctor roll coating, gravure coating, flexography, lithography, reverse-roll coating, slot-die coating, silkscreening and decalcomania.

15. The temperature indicating material of claim 11 wherein said temperature indicating composition is coated on said support in a pattern that appears upon exposure to saturated steam at 250° F.

16. A method for recording exposure to saturated steam at 250° F. and 15 psi for a minimum of twenty minutes comprising the steps of:

providing a temperature indicating material comprising a support coated on at least one surface with a composition comprising a dispersion in an aqueous binder of a color changing electron donating compound having a melting point greater than 300° F. and a polymeric electron accepting phenolic resin reactive with said electron donating compound to produce a visible and permanent color change and having a $T_g$ greater than 270° F. and non-volatility such that coatings containing said composition are stable upon exposure to dry heat at 284° F. for thirty minutes yet produce a fully developed visible and permanent color change when subjected to saturated steam at 250° F. for twenty minutes;

exposing said material to an elevated temperature condition; and evaluating the color of said composition coated on said support to determine whether said composition was exposed to saturated steam at 15 psi or greater and temperatures of 250° F. and higher for twenty or more minutes.

17. A method for recording exposure to saturated solvent vapors at 275° F. and 20 psi for a minimum of twenty minutes, comprising the steps of:

providing a temperature indicating material comprising a support coated on at least one surface with a composition comprising a dispersion in an aqueous binder of a color-changing electron donating compound having a melting point greater than 300° F. and a polymeric electron accepting phenolic resin reactive with said electron donating compound to produce a visible and permanent color change and having a $T_g$ greater than 270° F. and non-volatility such that coatings containing said composition are stable upon exposure to dry heat at 284° F. for thirty minutes yet produce a fully developed visible and permanent color change when subjected to saturated solvent vapors at 275° F. for twenty minutes;

exposing said material to an elevated temperature condition; and evaluating the color of said composition coated on said support to determine whether said composition was exposed to saturated solvent vapors at 20 psi or greater and temperatures of 275° F. or higher for twenty or more minutes.

18. The method of claim 17, wherein said solvent vapors consist essentially of less than 15 percent water, approximately 0.25 percent formaldehyde and one or more alcohols selected from the group consisting of ethanol, isopropanol and methanol.

* * * * *

UNITED STATES PATENT AND TRADEMARK OFFICE
CERTIFICATE OF CORRECTION

PATENT NO. : 5,340,537
DATED : August 23, 1993
INVENTOR(S) : Barrett

It is certified that error appears in the above-indentified patent and that said Letters Patent is hereby corrected as shown below:

On the Cover Page, [73], "South Planfield" should read --South Plainfield--.

Column 11, line 5, "phenolic accepting resin" should read --accepting phenolic resin--.

Signed and Sealed this

Eighth Day of November, 1994

Attest:

BRUCE LEHMAN

Attesting Officer      Commissioner of Patents and Trademarks